United States Patent [19]

May et al.

[11] Patent Number: 4,517,688

[45] Date of Patent: May 21, 1985

[54] ARTIFICIAL LEG FOR OCCASIONAL USE

[75] Inventors: Denis R. W. May, Esher; James N. Hiddleston, London, both of England

[73] Assignee: J. D. Hanger & Company Limited, London, England

[21] Appl. No.: 519,782

[22] Filed: Aug. 2, 1983

[30] Foreign Application Priority Data

Aug. 2, 1982 [GB] United Kingdom ............... 8222242

[51] Int. Cl.³ ............................................. A61F 1/68
[52] U.S. Cl. ........................................... 3/2; 3/17 R; 128/82; 128/84 R; 128/87 R
[58] Field of Search .............. 3/4, 2, 16, 17 R, 17 SS, 3/18, 19, 20, 21; 128/82

[56] References Cited

U.S. PATENT DOCUMENTS

| 584,004 | 6/1897 | Lyons | 3/8 |
| 3,889,301 | 6/1975 | Bonner, Sr. | 3/21 |
| 4,128,903 | 12/1978 | Marsh et al. | 3/21 |
| 4,300,245 | 11/1981 | Saunders | 3/21 |

Primary Examiner—Richard J. Apley
Assistant Examiner—D. J. Isabella
Attorney, Agent, or Firm—Pollock, Vande Sande and Priddy

[57] ABSTRACT

An inflatable lower limb prosthesis comprises an outer cover of relatively inextensible material defining the shape of a leg prosthesis and having a pad of rigid material at its lower end defining the shape of a foot. An inner member of independently inflatable compartments welded together comprises a shin compartment contacting the rigid pad and of upwardly convergent profile, an inner spacer compartment between the upper end of the shin compartment and the patient's stump and an annular socket compartment that surrounds the patient's stump and extends downwardly in overlapping relation around the upper end of the shin compartment to resist bending of the prosthesis at the false joint at the patient's stump.

1 Claim, 1 Drawing Figure

U.S. Patent May 21, 1985 4,517,688
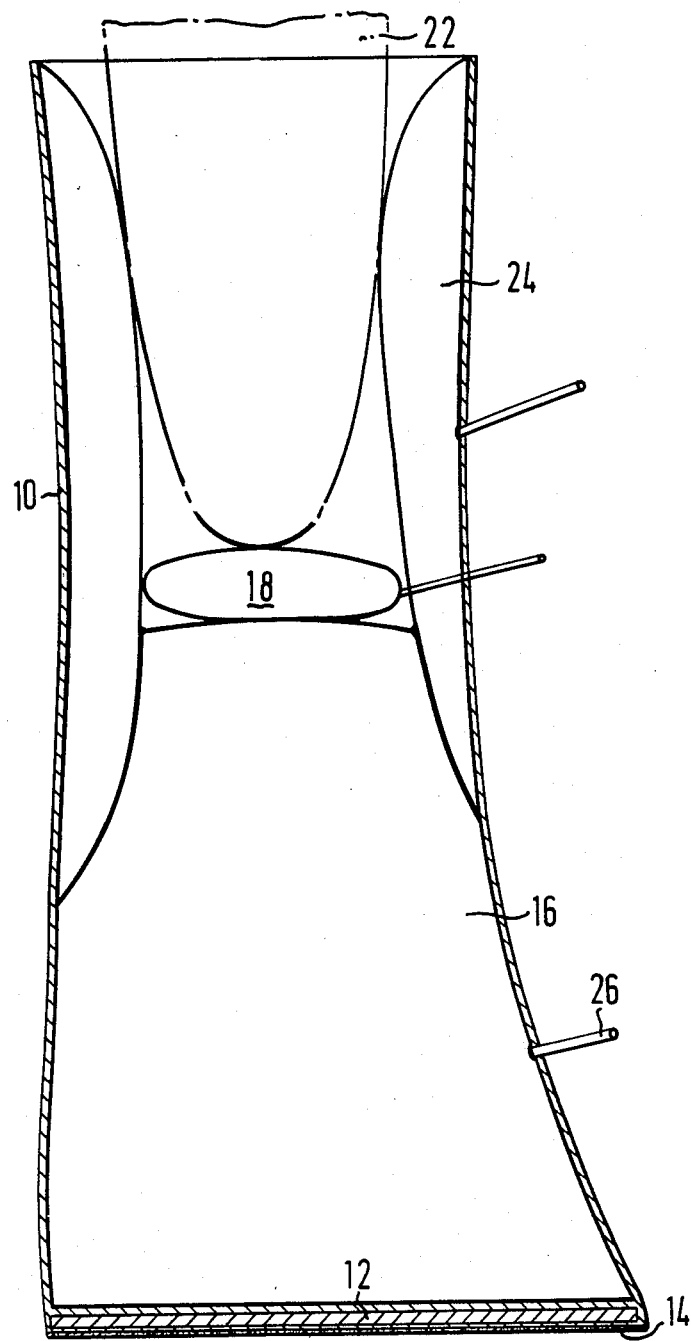

ARTIFICIAL LEG FOR OCCASIONAL USE

FIELD OF THE INVENTION

The present invention relates to an inflatable artificial leg.

BACKGROUND OF THE INVENTION

The use of inflatable splints to treat lower limb injury such as skiing accidents is described in UK Patent Specifications Nos. 970890, 1103181 and 1171361 and in U.S. Pat. No. Re. 26,046. But the purpose of such splints when applied to a lower limb is to immobilize it while the patient is transported to hospital and they neither are nor are intended as capable of supporting the weight of the patient and assisting walking.

SUMMARY OF THE INVENTION

It is an object of the invention to provide a lower limb prosthesis for occasional use by amputees, eg. in showers, that can be collapsed into a very compact state.

The invention provides a lower limb prosthesis comprising means defining a ground contacting lower surface, inflatable stump support means extending upwardly from the lower surface, and inflatable socket means for surrounding the stump and so connected to said support means to provide stiff support between the stump and the ground.

The invention also provides an inflatable lower limb for use by amputees comprising: an outer cover of relatively inextensible material defining the shape of the leg and having a pad of rigid material at its lower end defining the shape of the foot; and an inner member of independently inflatable compartments welded together comprising a shin compartment contacting the rigid pad and being of upwardly convergent profile, an inner spacer compartment between the upper end of the shin compartment and the patient's stump, and an annular socket compartment that surrounds the patient's stump and the shin compartment and extends downwardly in overlapping relation around the upper end of the shin compartment to resist bending of the limb at the false joint at the patient's stump.

DESCRIPTION OF PREFERRED EMBODIMENT

The inner member and the outer cover are both of waterproof material and it is envisaged that one main use of the lower limb will be when the wearer wishes to take a shower. Because it is wholly of flexible plastics sheet or textile material except for the rigid pad, it may be rolled up into a very compact form and can be readily packed into the wearer's luggage.

BRIEF DESCRIPTION OF THE DRAWING

An embodiment of the invention will now be described by way of example only with reference to the accompanying drawing which is a diagrammatic vertical sectional view of an inflatable artificial leg.

DETAILED DESCRIPTION OF THE PREFERRED EMBODIMENT

In the drawing, the shape of the leg is defined by an outer casing 10 of relatively inextensible material such as a polyurethane coated woven nylon fabric. At its lower end is a base pad 12 of rigid material sealed into a water-tight pocket bonded to the outer casing 10. A sole 14 of rubberized anti-skid sheet material is bonded to the base of the outer cover.

In outer casing 10 fits an inflatable inner member formed of three independent compartments welded together. A shin compartment 16 fits immediately above the baseplate 12 and tapers inwardly as shown. Above the shin compartment is an inner spacer compartment 18 that may be inflated to a desired height appropriate to the length of the wearer's stump 22. An annular socket compartment 24 surrounds the stump 22, the inner space compartment 18 and the upper end of the shin compartment which it overlaps as shown. The reason for this overlap is to avoid the effects of the false joint between the inflatable leg and the wearer's stump which if insufficiently supported by a rigid tube structure is prone to collapse.

In use the wearer first inflates the shin compartment 16 through tube 26. Then he inserts his stump into the socket compartment 24 and inflates the inner spacer compartment 18 until it reaches the required height to support his stump. Finally he inflates the socket compartment 24. After use, air is expelled from the three compartments and the leg can be rolled up about the base pad 12 to a small size that is convenient for packing.

We claim:

1. An inflatable lower limb for use by amputees comprising: an outer cover of relatively inextensible material defining the shape of the leg and having a pad of rigid material at its lower end defining the shape of the foot; and an inner member within and separate from said relatively inextensible outer cover and comprisng a plurality of independently inflatable compartments welded together, said inner member including an inflatable shin compartment contacting the rigid pad and being of upwardly convergent profile, a separately inflatable inner spacer compartment between the upper end of said shin compartment and the patient's stump, and a further separately inflatable annular socket compartment that surrounds the patient's stump and said shin compartment and extends downwardly in overlapping relation around the upper end of said shin compartment to resist bending of the limb at the false joint at the patient's stump.

* * * * *